United States Patent
Bush et al.

(10) Patent No.: US 10,857,253 B2
(45) Date of Patent: Dec. 8, 2020

(54) MICROFLUIDIC EJECTION ELEMENT AND METHOD OF OPERATION OF A MICROFLUIDIC EJECTION ELEMENT HAVING A SIMPLIFIED INTERFACE

(71) Applicant: The Procter & Gamble Company, Cincinnati, OH (US)

(72) Inventors: Stephan Gary Bush, Liberty Township, OH (US); John Glenn Edelen, Lexington, KY (US); Viren N. Patel, Lexington, KY (US); Michael Anthony Marra, III, Lexington, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/045,791

(22) Filed: Jul. 26, 2018

(65) Prior Publication Data
US 2020/0031119 A1     Jan. 30, 2020

(51) Int. Cl.
*A61L 9/14*     (2006.01)
*B41J 2/045*    (2006.01)
*A61L 9/03*     (2006.01)

(52) U.S. Cl.
CPC .................. *A61L 9/14* (2013.01); *A61L 9/03* (2013.01); *A61L 2209/11* (2013.01); *A61L 2209/132* (2013.01); *B41J 2/0458* (2013.01)

(58) Field of Classification Search
CPC ........ A61L 9/14; A61L 9/03; A61L 2209/132; A61L 2209/11; B41J 2/0458
See application file for complete search history.

(56) References Cited

U.S. PATENT DOCUMENTS

| | | | |
|---|---|---|---|
| 2002/0186265 A1* | 12/2002 | Schloeman | B41J 2/04543 347/12 |
| 2004/0085399 A1 | 5/2004 | Ahne | |
| 2009/0033702 A1 | 2/2009 | Clark | |

FOREIGN PATENT DOCUMENTS

| | | |
|---|---|---|
| EP | 1314562 A2 | 5/2003 |
| JP | H10202851 A | 8/1998 |
| WO | WO2015195996 A1 | 12/2015 |

OTHER PUBLICATIONS

Case 15314 PCT Search report; Application No. PCT/US/2019/040457; dated Sep. 23, 2019; 14 Pages.

* cited by examiner

*Primary Examiner* — Geoffrey S Mruk
(74) *Attorney, Agent, or Firm* — Abbey A. Lopez

(57) ABSTRACT

A control circuit for a thermally-activated microfluidic ejection element and a method of dispensing a fluid composition from the same is provided. The thermally-activated microfluidic ejection element includes a plurality of nozzles and a thermal actuator associated with each nozzle, and a control circuit that includes: a logic circuit that increments through a pre-determined sequence, wherein the sequence is defined by the physical layout of the thermally-activated microfluidic ejection element; a first input in electrical communication with the logic circuit; a second input in electrical communication with each thermal actuator, wherein the first input and second input are used to select and energize each thermal actuator on the thermally-activated microfluidic ejection element.

12 Claims, 20 Drawing Sheets

PRIOR ART

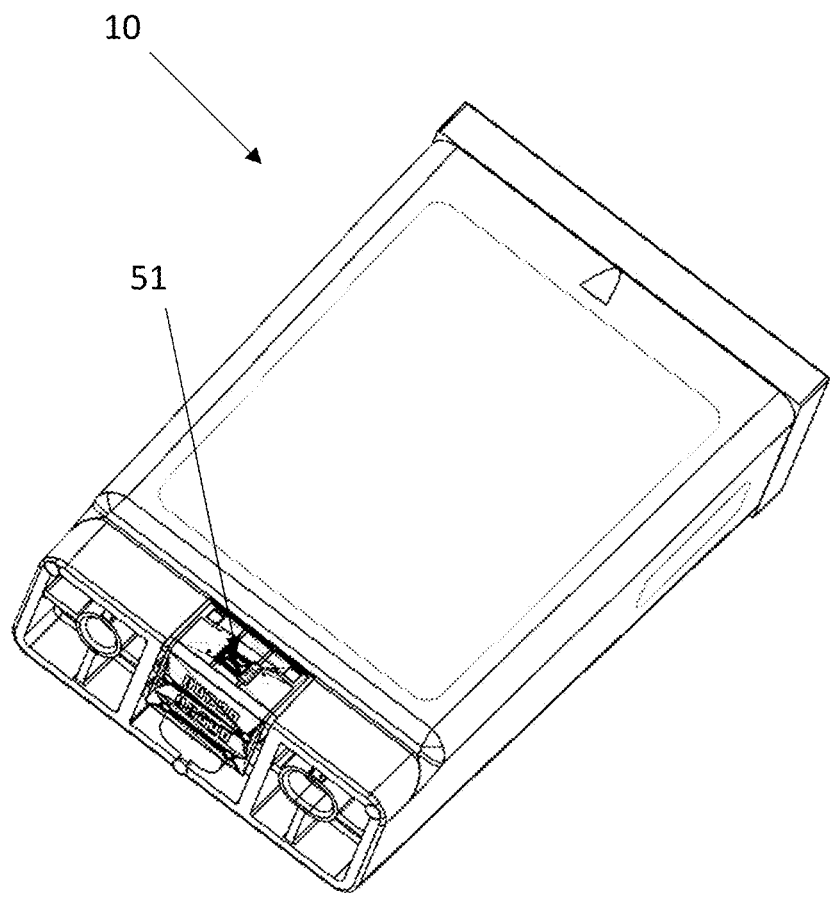
Fig. 10
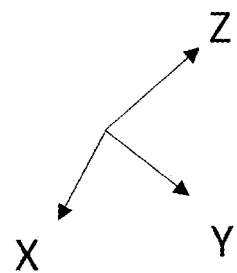

MICROFLUIDIC EJECTION ELEMENT AND METHOD OF OPERATION OF A MICROFLUIDIC EJECTION ELEMENT HAVING A SIMPLIFIED INTERFACE

FIELD

The present disclosure is directed to a microfluidic ejection element and a method of operation of a microfluidic ejection element, and, more particularly, is directed to a microfluidic ejection element and a method of operation of a microfluidic ejection element having a simplified interface optimized for dispensing a fluid composition into the environment.

BACKGROUND

Consumer and industrial inkjet printing is well known. In such applications, it is known in the application that the individual nozzles in the ejection chip should be individually addressable so that they can be actuated on demand. As the ejection head is passed over the media to be printed, an image is formed that requires a certain data rate from the control element that controls the actuation of the nozzles. This data rate may be achieved through a combination of a number of signal lines and a signaling rate where digital data are passed into the ejection chip. Together, the signal lines and signaling rate form a communications channel that must be capable of passing enough information to form the required image while the ejection head is traveling at the required speed.

A compromise must be achieved when designing a printing system where the number of signal lines is not excessive, increasing the size and complexity of the system. If the number of signal lines is small, and the communication protocol with the ejection chip is not efficient, the signaling rate into the chip can become so high that it is not possible to maintain acceptable signal integrity. The example below illustrates the choices made when designing such printing systems.

For ink-jet printing applications, the microfluidic ejection element is optimized to produce high resolution images while minimizing overall print time. For these reasons the thermal actuators (i.e., heaters) on the ejection chip will typically be arrayed to provide a half inch print swath or greater with thermal actuator to thermal actuator spacing at 42.3 μm (1/600 inch) or 21.2 μm (1/1200 inch).

As an illustration, the nozzle placement and addressing architecture of a 16.9 mm (two-thirds inch), 47.2 drops per millimeter (1200 drops per inch) printhead with a total of 800 thermal actuators is described.

FIG. 1 shows the thermal actuator placement for this prior art example. As shown, the thermal actuators on one side of the fluid via are vertically spaced at 42.3 μm (1/600 inch) with the thermal actuators on the opposite side also spaced at 1/600 inch but shifted vertically by 21.2 μm (1/1200 inch). This allows for single pass printing to place a drop of ink at each point on a 21.2 μm (1/1200 inch) vertical pitch.

If the desired print pattern resolution is 21.2 μm (1/1200 inch) vertical and 42.3 μm (1/600 inch) horizontal, one must now consider how to address and actuate thermal actuators as the head moves in the horizontal direction.

FIG. 2 shows a 21.2 μm by 21.2 μm (1/1200 by 1/1200 inch) grid with one example of an acceptable prior-art drop placement pattern. If one considers HTR1 in this example one can see that it is actuated after every 42.3 μm (1/600 inch) of printhead movement. To optimize print speed, it is desired to actuate the thermal actuator at the highest frequency allowed by fluidic cartridge characteristics. For this example, we will assume an 18 kHz thermal actuator. Considering the relationship of:

velocity=distance/time, the calculated printhead speed is determined to be 762 mm/second (30 inches/second).

With these parameters defined, for a printhead moving at 762 mm/second (30 inches/second), all 800 thermal actuators must be addressed and actuated in 42.3 μm (1/600 inch) of travel. In this example, the time to address all actuators would be 55.55 μs. If each thermal actuator was addressed individually the time slice for each actuator would be 55.55 μs/800=69.4 ns. For thermal microfluidic ejection elements, this time is inadequate to eject the droplet, as the time required to nucleate a fluid is typically greater than 400 ns.

For this reason, and in order to reduce the data rate required, an address matrix is defined which allows for multiple thermal actuators to be actuated in the same time slice. The address matrix is typically defined as groups of thermal actuators referred to as Primitives (P) and Addresses (A).

For the 800-thermal actuator example an acceptable address matrix may be 20P×40A=800. This would now define the time slice as 55.55 μs/40=1.39 μs.

For many applications this is an acceptable nucleation time. However, for some thermal print systems it is desirable to provide the ejection energy in two separate pulses to improve the velocity of the ejected drop. In this case, the time slice would need to be further increased. This can be done by changing the ratio of the P×A address matrix. One aspect to consider if the number of Primitives P groups is increased is that this also increases the amount of simultaneous current required for the thermal thermal actuators. For this example, the number of simultaneous fires at 20 is fixed so the address matrix will be changed by decreasing Addresses A to 20.

To allow more flexibility in how the energy is applied to the actuators, (overlapped, interlaced etc.) a third variable is added to the address matrix, Fire (F). In this example the address matrix is now defined as 20P×20A×2F=800.

FIG. 3 shows a timing diagram for a final prior-art address A matrix. As shown, the number of addresses A has been further decreased by the introduction of a fourth variable Extended Address (EA). In this case, it is not done to increase the duration of the time slice but to reduce the width of the address bus required on the silicon chip. Thus, the final address matrix is:

$$20P \times 5A \times 2F \times 4EA = 800.$$

Also shown in FIG. 3, there is the addition of two cycles, D1 and D2, where no thermal actuators are actuated. This is a typical practice when using a moving printhead. In the case that feedback from the printer indicates that the printhead is moving too fast or too slow these time periods, dead cycles are inserted to allow for printhead location correction and timing synchronization.

FIG. 4 represents one possible prior art grouping of primitives P along the thermal actuator array. Each primitive P represents 40 thermal actuators. In each of the 40 time slices, the number of thermal actuators actuated is determined by the number of Primitives P selected. This can be 0 to 20.

The example embodiment shown in FIGS. 1 to 4 demonstrates the design constraints when considering a traditional prior-art print head system. In the printing application, the address matrix is defined by the spatial pattern of the thermal actuators, desired print resolution, print speed and the fluidic response of the thermal actuators. In a printing application the primitive P and address A data is often shifted into the printhead using two or more serial data inputs.

FIG. 5 illustrates a prior art timing diagram for serially loading print data into the printhead. This configuration requires clock (CLK), data (ADATA/PDATA), load (LOAD) and fire (FIRE1, FIRE2). Not shown is a reset (RST) signal used to clear the chip registers. In this configuration the chip requires a total of 7 digital inputs.

During each time slice the printer will send a new ADATA and PDATA input stream. To shift the data into the chip one clock edge is required for each bit of data. The LOAD signal is used to latch data into internal registers after the data stream is complete. Once the ADATA and PDATA for the current time slice is latched, the FIRE1 and FIRE2 signals are used to activate the thermal actuators.

As shown in the timing diagram, the data for the next time slice is being clocked into the chip while the thermal actuators for the previous time slice are activated.

A single ADATA or PDATA register may be 40 bits or longer. To achieve reasonable print speeds the CLK rate is typically 16 MHz to 48 MHz.

As shown in this example, a microfluidic ejection element having the capability to print an image may have considerable complexity and require significant computing and input/output speeds.

Another dispensing application, apart from printing ink on media as described above, is one where fluid is dispersed into the environment, such as dispersing a liquid composition into the air. For such an application, it is not necessary to form an image, nor is it required to address particular nozzles at precise times and locations.

In such a dispensing application, the critical performance parameter is the mass dispense rate. This is determined by the number of nozzles and the frequency at which they can be fired. Since it is not necessary to form an image as in a printing application, the computing requirements for the controlling device are much less demanding. In fact, when dispensing into the environment, it is desirable to have a very simple controlling device, which may comprise, for example, a low cost 8-bit microcontroller. For this configuration, a simple interface to the ejection chip is desirable for cost and complexity reasons.

SUMMARY

In order to address one or more of the outages of the prior art, the present invention provides the following methods and microfluidic ejection elements:

A. A method of delivering a fluid composition from a thermally-activated microfluidic ejection element, the thermally-activated microfluidic ejection element comprising a plurality of nozzles and a thermal actuator associated with each nozzle, the method comprising:
  connecting the thermally-activated microfluidic device to a power source;
  delivering a first electrical pulse to a first input that selects a thermal actuator from a pre-determined sequence, wherein the pre-determined sequence is defined by the physical layout of the thermally-activated microfluidic device;
  supplying a second electrical pulse of a well-defined width to a second input to activate the selected thermal actuator; and
  ejecting a fluid composition from the nozzle associated with the selected thermal actuator.

B. The method of Paragraph A further comprising the step of reading a memory bit from a sequence of memory bits, wherein the value of the memory bit is presented on an output pin.

C. The method of Paragraph A or Paragraph B further comprising the step of writing a memory bit currently selected from a sequence of memory bits.

D. The method of Paragraph C, wherein the number of memory bits and the number of nozzles are not equal.

E. The method of any of Paragraphs A through D, wherein the first electrical pulse is delivered by a first input, wherein the first input is in electrical communication with a ripple counter and an address decoder.

F. The method of any of Paragraphs A through E, wherein the pre-determined sequence of nozzles is arranged on the thermally-activated microfluidic ejection element such that nozzles that are numerically adjacent in the pre-determined sequence are not physically adjacent.

G. The method of any of Paragraphs A through F, wherein the duration of the second electrical pulse corresponds to the time that the thermal actuator associated with the selected nozzle is activated.

H. The method of any of Paragraphs A through G, wherein the first electrical pulse selects two or more thermal actuators from a pre-determined sequence, and wherein the second electrical pulse activates the two or more thermal actuators, and wherein the step of ejecting a fluid composition from the nozzle associated with the thermal actuator further comprising ejecting a fluid composition from the nozzles associated with the two or more thermal actuators.

I. The method of any of Paragraphs A through H further comprising the steps of:
  raising the temperature throughout the thermally-activated microfluidic ejection element with a substrate heater that is separate from the thermal actuator associated with the nozzle.

J. A thermally-activated microfluidic ejection element, the thermally-activated microfluidic ejection element comprising a plurality of nozzles and a thermal actuator associated with each nozzle, and a control circuit, the control circuit comprising:
  a logic circuit that increments through a pre-determined sequence, wherein the pre-determined sequence is defined by the physical layout of the thermally-activated microfluidic ejection element;
  a first input in electrical communication with the logic circuit; and
  a second input in electrical communication with each thermal actuator,
  wherein the first input and second input are used to select and energize each thermal actuator on the thermally-activated microfluidic ejection element.

K. The thermally-activated microfluidic ejection element of Paragraph J further comprising a plurality of memory cells, wherein a single memory cell is selected by the logic circuit, and wherein the binary state of the selected memory cell is accessible through an output.

L. The thermally-activated microfluidic ejection element of Paragraph K, wherein the number of memory cells and the number of nozzles are not equal.

M. The thermally-activated microfluidic ejection element of any of Paragraphs J through L, wherein the logic circuit comprises a ripple counter and an address decoder.

N. The thermally-activated microfluidic ejection element of any of Paragraphs J through M, wherein the predetermined sequence is configured such that nozzles that are physically adjacent are not fired in sequence.

O. The thermally-activated microfluidic ejection element of any of Paragraphs J through N, wherein the thermally-activated microfluidic ejection element comprising a first plurality of nozzles and a second plurality of nozzles, wherein the first plurality is in fluid communication with a first fluid composition disposed in a first reservoir, wherein the second plurality is in fluid communication with a second fluid composition disposed in a second reservoir, wherein the first and second fluid compositions are different.

P. The thermally-activated microfluidic ejection element of any of Paragraphs J through O further comprising:
 a substrate heater configured to raise the temperature throughout the thermally-activated microfluidic ejection element, wherein the substrate heater is separate from the thermal actuator associated with the nozzle; and
 a temperature sensor.

BRIEF DESCRIPTION OF THE DRAWINGS

FIG. 10 is a perspective view of an exemplary cartridge having a microfluidic ejection element.

DETAILED DESCRIPTION

Figure 1:
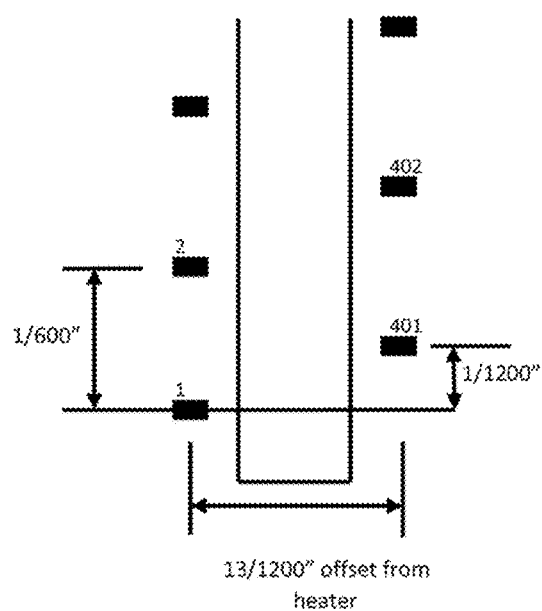
FIG. 1 is a schematic, plan view of a portion of a prior art microfluidic ejection element, showing thermal actuator placement.
Figure 2:
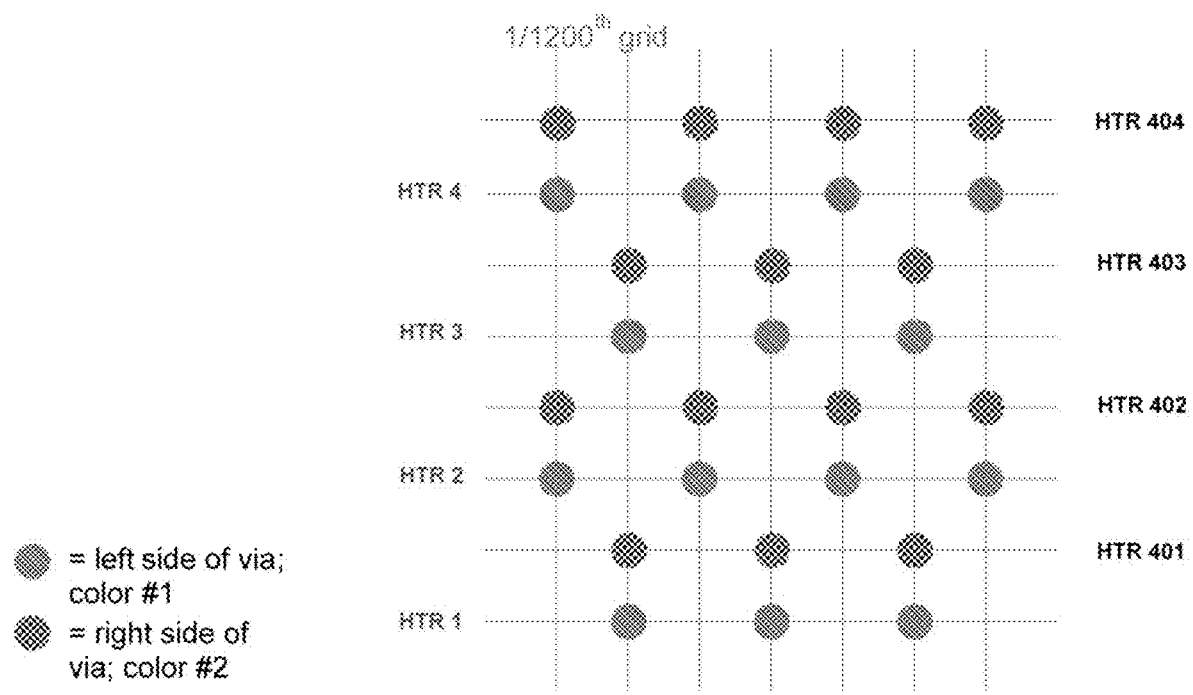
FIG. 2 is a 21.2 μm by 21.2 μm (1/1200 by 1/1200 inch) grid with one example of an acceptable prior-art drop placement pattern
Figure 3:
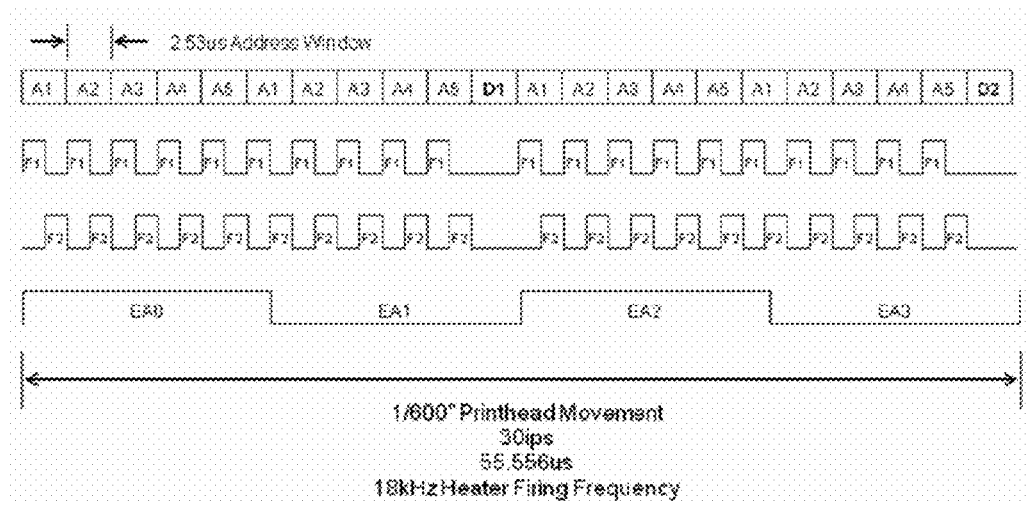
FIG. 3 is a timing diagram for a final prior-art address A matrix.
Figure 4:
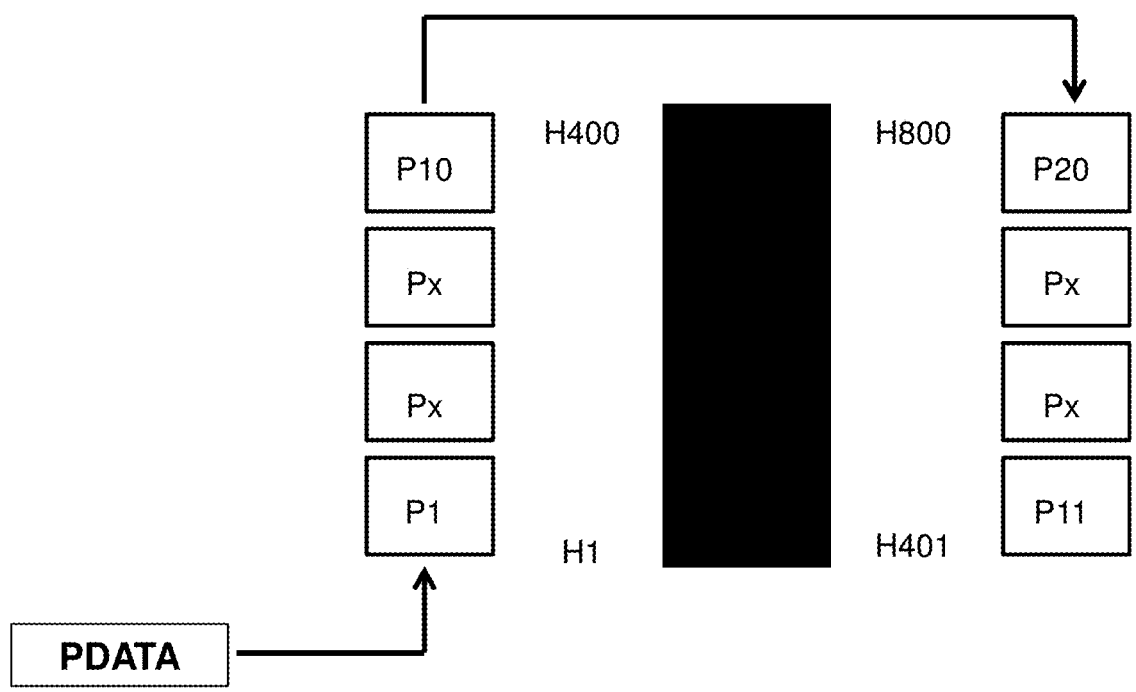
FIG. 4 is a diagram illustrating one possible prior art grouping of primitives P along the thermal actuator array.
Figure 5:
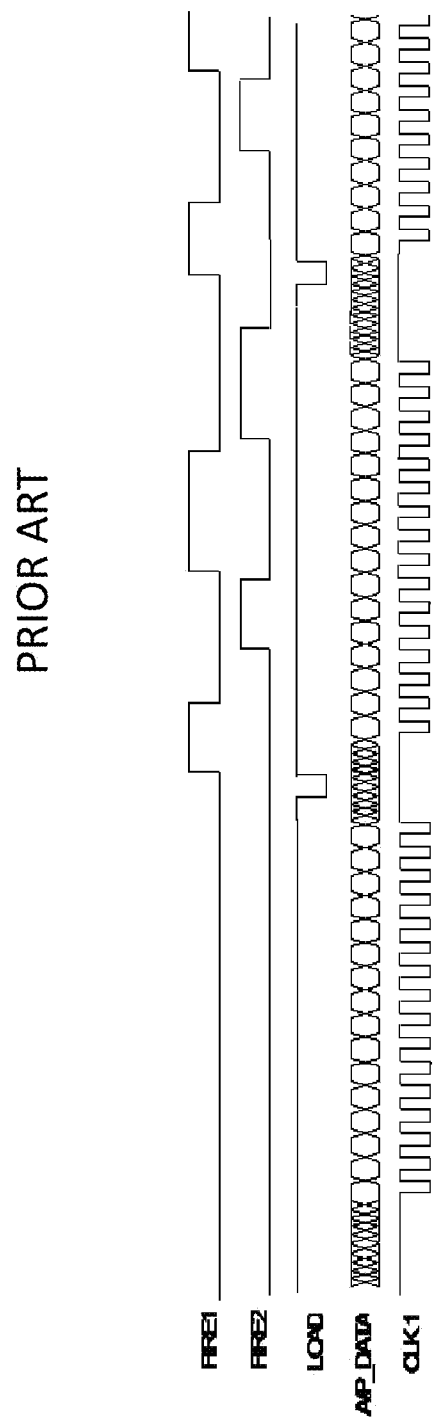
FIG. 5 is a prior art timing diagram for serially loading print data into a printhead.
Figure 6:
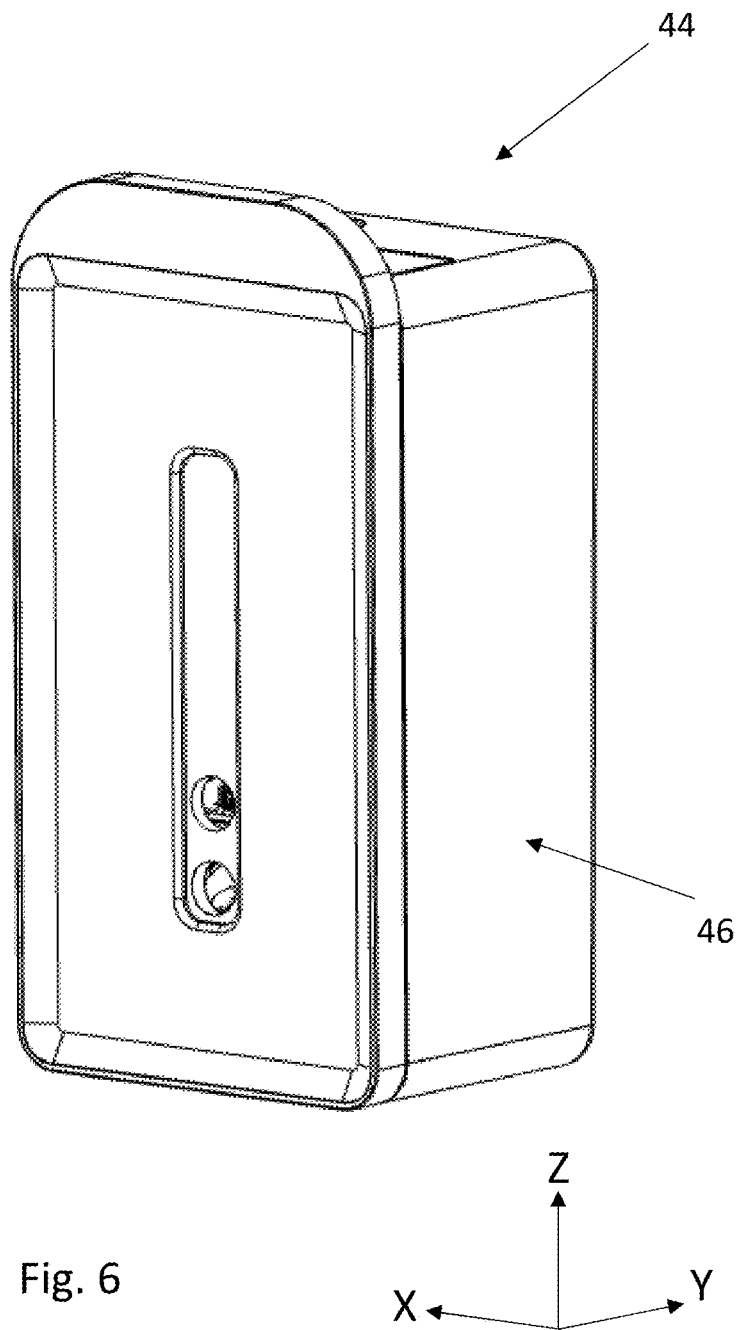
FIG. 6 is a front, perspective view of an exemplary microfluidic delivery device.
Figure 7:
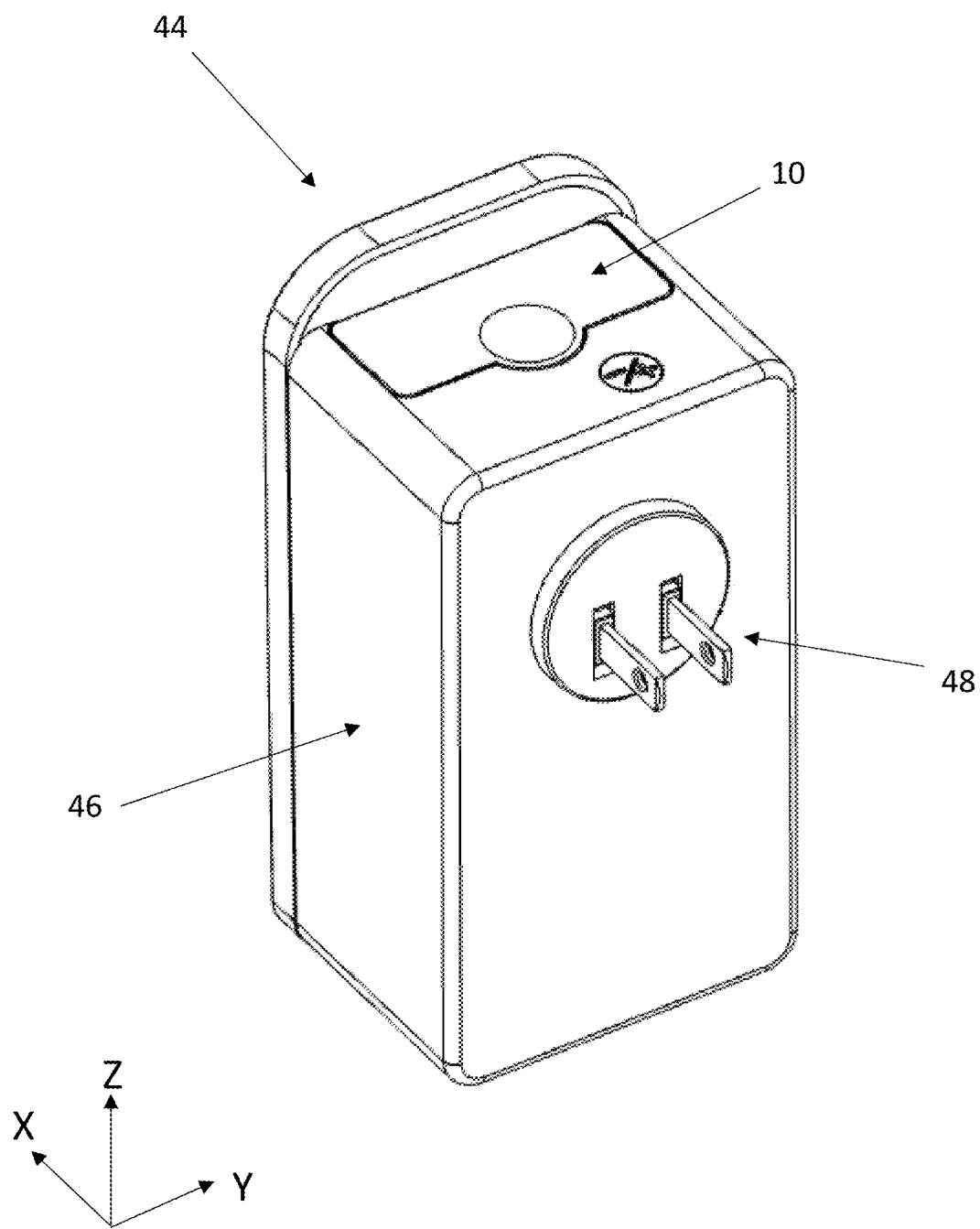
FIG. 7 is a back, perspective view of an exemplary microfluidic delivery device.
Figure 8:
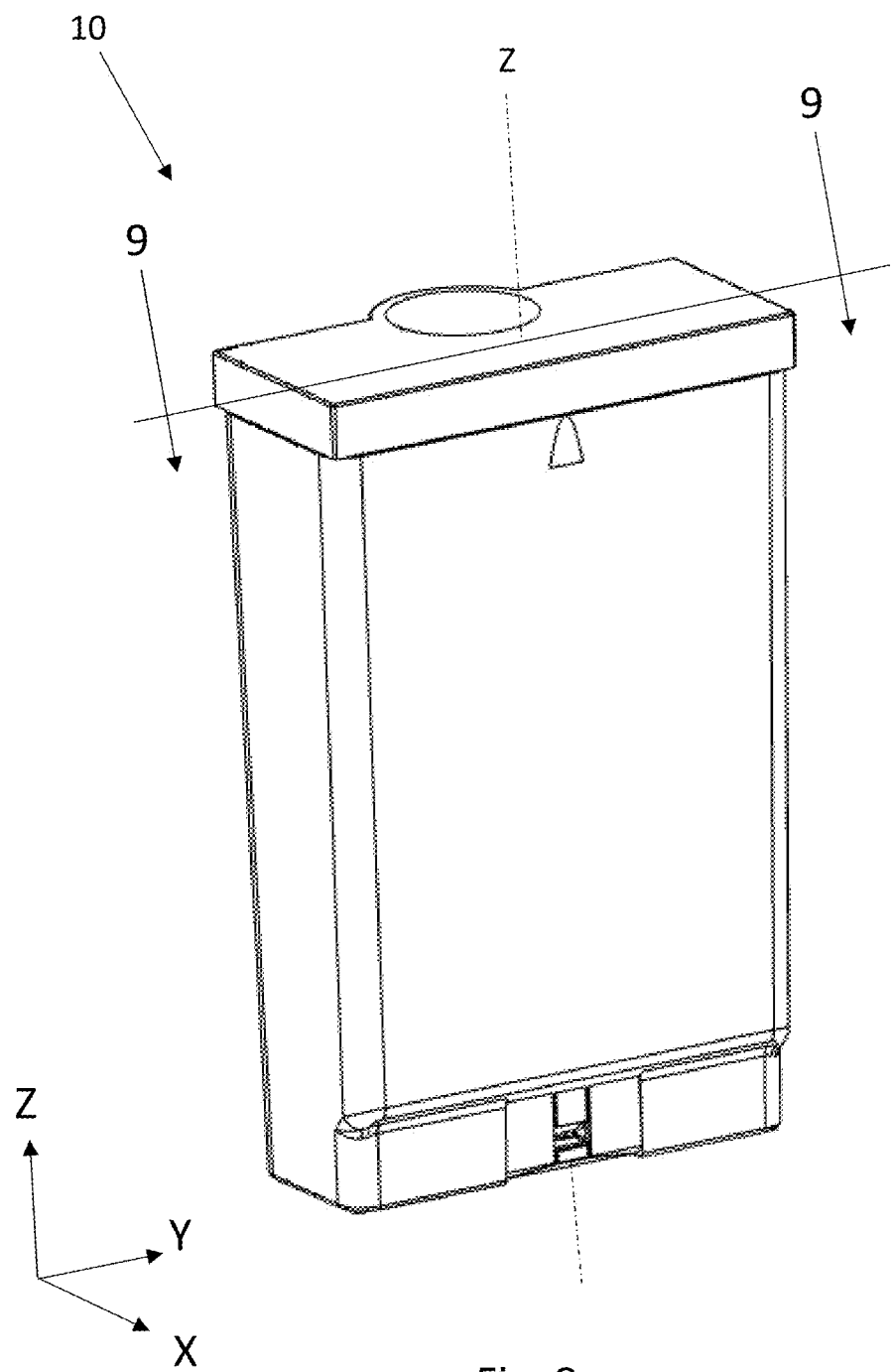
FIG. 8 is a perspective view of an exemplary cartridge.
Figure 9:
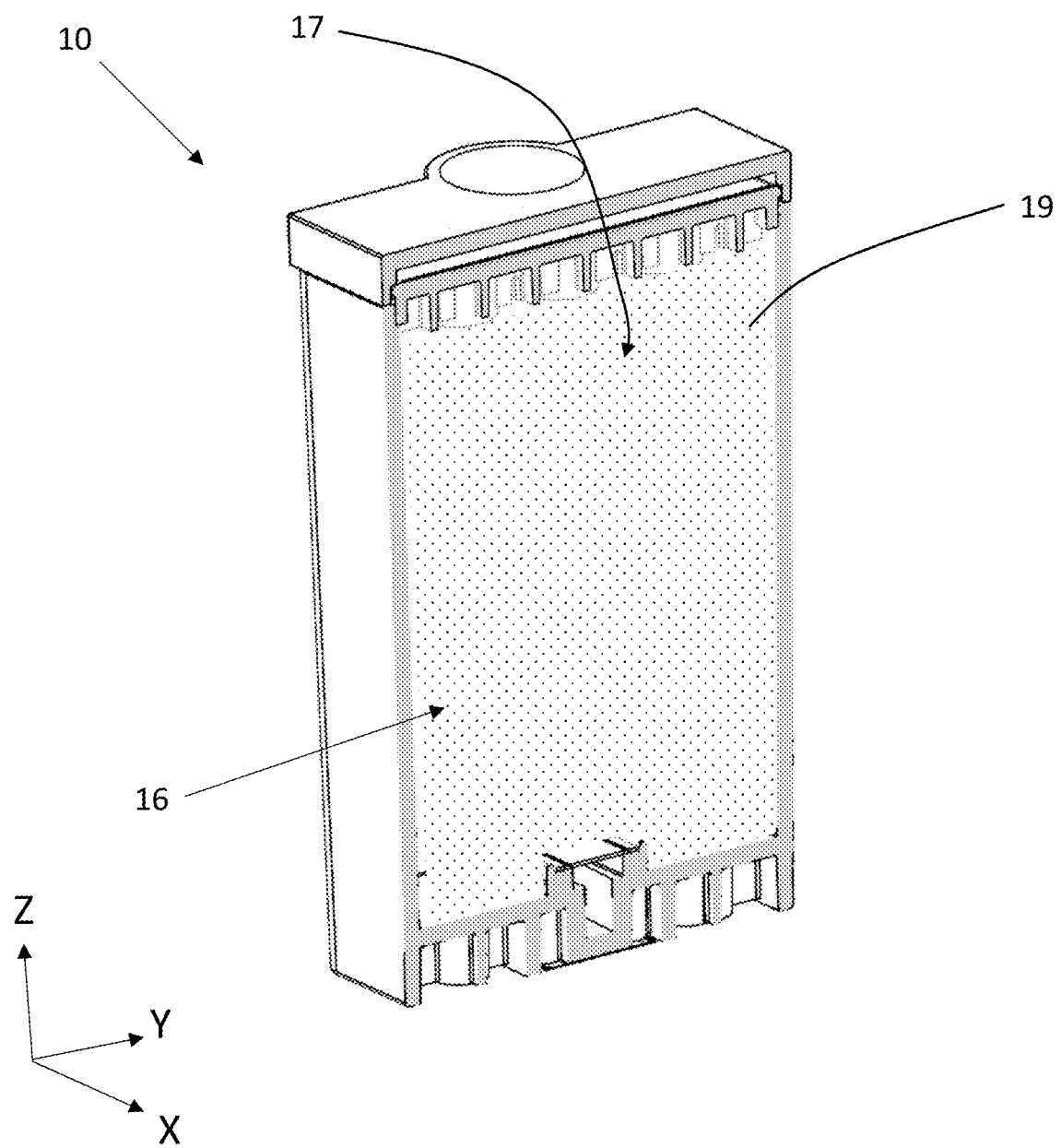
FIG. 9 is a sectional view of FIG. 8 taken along lines 9-9.

The invention described here comprises a microfluidic ejection element and its method of use which implement a simplified interface optimized for dispensing a fluid composition into the environment, such as the air. For dispensing a fluid composition into the air, it is not necessary to individually select and fire nozzles from distinct positions within the nozzle array. Therefore, the microfluidic ejection element of the present disclosure does not provide a means to address a particular nozzle or nozzles in a single time cycle.

The fluid composition may, for example, include inks, dyes, pigments, adhesives, curable compositions, optically activated compounds, metal oxides, bleaching agents, texture reducing polymers, silicones, stains, paints, surfactants, cleaners, malodor reducing agents, lubricants, fillers, perfumes, scents, polymers, polymeric additives, particles, optical modifiers, optical matchers, and other actives such as antibacterial and antimicrobials, and combinations of these or other materials, some of which are further described herein.

With reference to FIGS. 6-10, a microfluidic ejection element 51 may be a part of a cartridge 10. The cartridge 10 may be configured to be releasably connectable with a microfluidic delivery device 44. The microfluidic delivery device 44 may comprise a housing 46 and a power source 48. The housing 46 may receive all or a portion of the cartridge 10. The receptacle may receive a portion of the cartridge 10 or the cartridge 10 may be completely disposed within the receptacle.

The receptacle of the housing may include electrical contacts that are configured to electrically connect with the electrical contacts of the cartridge 10.

The cartridge 10 may include a reservoir 16 for containing a fluid composition 19. The reservoir 16 of the cartridge 10 may contain from about 5 mL to about 50 mL of fluid composition, alternatively from about 10 mL to about 30 mL of fluid composition, alternatively from about 15 mL to about 20 mL of fluid composition. The reservoir 16 can be made of any suitable material for containing a fluid composition. Suitable materials for the containers include, but are not limited to, plastic, metal, ceramic, composite, and the like. A cartridge may be configured to have multiple reservoirs, each containing the same or a different composition. The microfluidic delivery device may utilize one or more cartridges, each containing a separate reservoir.

The reservoir 16 may also contain a porous material 17 such as a sponge that creates a back pressure to prevent the fluid composition from leaking from the microfluidic ejection element when the microfluidic ejection element is not in operation. The fluid composition may travel through the porous material and to the microfluidic ejection element through gravity force and/or capillary force acting on the fluid composition. The porous material may comprise a metal or fabric mesh, open-cell polymer foam, or fibrous polyethylene terephthalate, polypropylene, or bi-components of fibers or porous wick, that contain multiple interconnected open cells that form fluid passages. The sponge may be free of a polyurethane foam.

Figure 11:
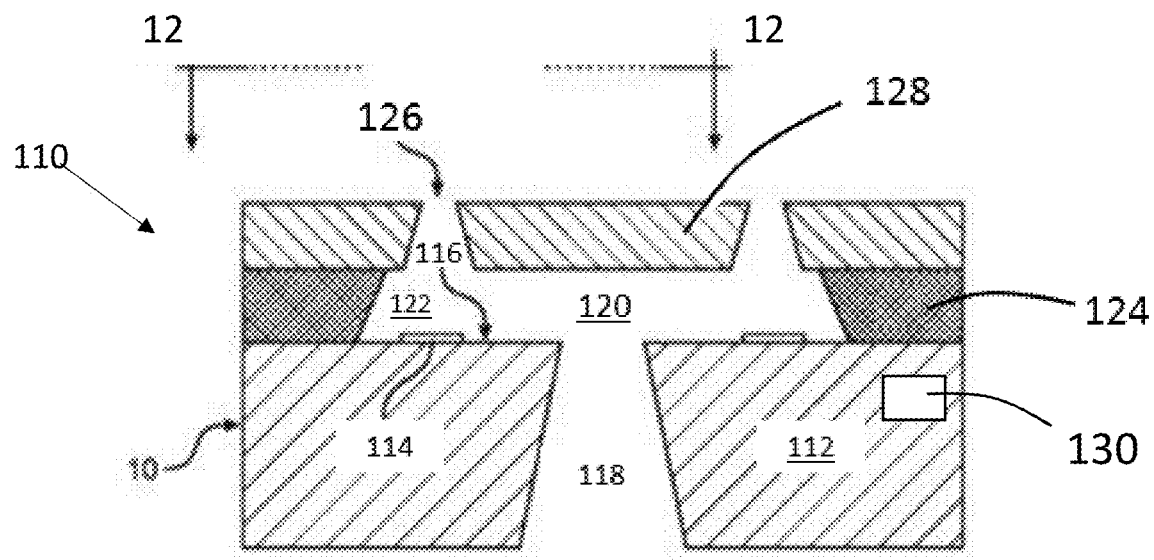
FIG. 11 is a sectional view of an exemplary microfluidic ejection element.
Figure 12:
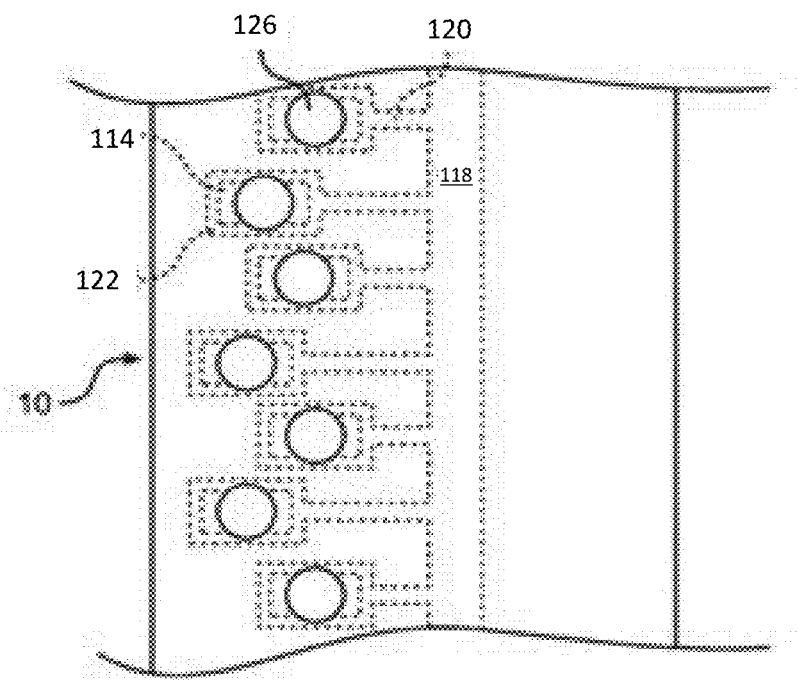
FIG. 12 is a plan view of a portion of a microfluidic ejection element.

With reference to FIGS. 10-12, the cartridge 10 may include a microfluidic ejection element 51. The microfluidic ejection element 51 may be in fluid communication with the fluid composition disposed in the reservoir.

The primary components of a microfluidic ejection element are a semiconductor substrate, a flow feature layer, and a nozzle plate layer. The flow feature layer and the nozzle plate layer may be formed from two separate layers or one continuous layer. The semiconductor substrate is preferably made of silicon and contains various passivation layers, conductive metal layers, resistive layers, insulative layers and protective layers deposited on a device surface thereof. Fluid ejection actuators in the semiconductor substrate generate rapid pressure impulses to eject the fluid composition from the nozzles. The fluid ejection actuators may be piezoelectric actuators or thermal actuators. Rapid pressure pulses may be generated by piezoelectric device that vibrates at a high frequency (e.g., micro mechanical actuation) or by a thermal actuator resistor (i.e., heater) that cause volatilization of a portion of a fluid composition within the fluid composition through rapid heating cycles (e.g., micro thermal nucleation). For thermal actuators, individual thermal actuator resistors are defined in the resistive layers and each thermal actuator resistor corresponds to a nozzle in the nozzle plate for heating and ejecting the fluid composition from the nozzle.

With reference to FIGS. 11 and 12, there is shown a simplified representation of a portion of a microfluidic ejection element 110. The microfluidic ejection element includes a semiconductor substrate 112 that may be a silicon semiconductor substrate 112 containing a plurality of fluid ejection actuators 114 such as piezoelectric devices or thermal actuator resistors formed on a device side 116 of the substrate 112 as shown in the simplified illustration of FIG. 11. In a microfluidic ejection element having piezo actuators as the fluid ejection actuators 114, the piezo actuator may be disposed adjacent the nozzle such as shown in FIG. 11 or may be disposed away from the nozzles and still transmit the pressure pulse to the fluid composition to be ejected from the nozzles. Upon activation of fluid ejection actuators 114, fluid supplied through one or more fluid supply vias 118 in the semiconductor substrate 112 flows through a fluid supply channel 120 to a fluid chamber 122 in a thick film layer 124 where the fluid is caused to be ejected through nozzles 126 in a nozzle plate 128. Fluid ejection actuators are formed on the device side 116 of the semiconductor substrate 112 by well-known semiconductor manufacturing techniques. Thick film layer 124 and nozzle plate 128 may be separate layers or may be one continuous layer.

The nozzle plate 128 may include about 4-200 nozzles 126, or about 6-120 nozzles, or about 8-64 nozzles. Each nozzle 126 may deliver about 0.5 to about 35 picoliters, or about 1 to about 20 picoliters, or about 2 to about 10 picoliters of a fluid composition per electrical firing pulse. Individual nozzles 126 may have of a diameter typically about 23 microns (5-50 microns). The flow rate of fluid composition released from the microfluidic ejection element 51 could be in the range of about 5 to about 70 mg/hour or any other suitable rate or range.

Figure 13:
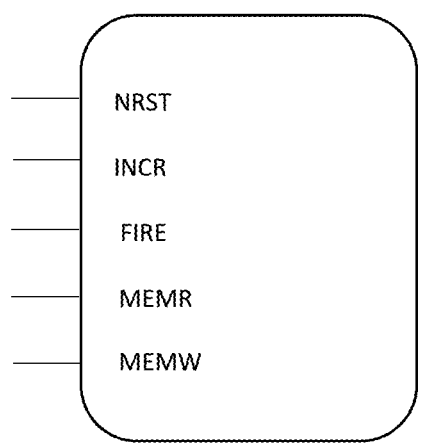
FIG. 13 is a diagram of an interface (showing logic signals only) to a microfluidic ejection element supporting its method of use which implements a simplified interface optimized for dispensing applications.

With reference to FIG. 13, there is shown the logical interface to the microfluidic ejection element supporting its method of use which implements a simplified interface optimized for dispensing applications. Additional interface elements needed to complete the physical interface (for example, power and/or analog signal connections) are omitted for clarity purposes only. For dispensing a fluid composition into the air, it is not necessary to individually select and fire nozzles from distinct positions within the nozzle array. Therefore, the microfluidic ejection element of the present disclosure does not provide a means to address a particular nozzle or nozzles in a single time cycle. Instead, a predetermined firing sequence is provided, which is determined at design time. Hereinafter, the collection of logical inputs/outputs and other connections (power and analog) will be referred to as an interface.

An exemplary embodiment of the invention is described. A microfluidic delivery element may comprise a semiconductor chip having a control circuit with an interface. The interface comprises a signal (NRST) that, when asserted, resets the logic of the chip to a known starting condition. The interface further comprises a signal (INCR) which causes the logic circuit within the microfluidic ejection element to select the next nozzle from a predetermined sequence. The pre-determined sequence is encoded in the chip at design time. The interface also comprises a signal (FIRE) which actuates the thermal actuator associated with the selected nozzle.

Figure 14:
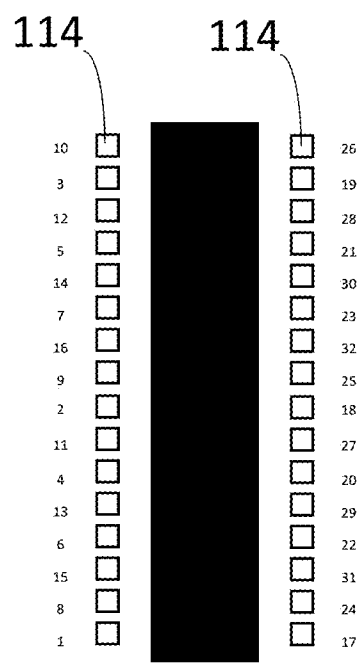
FIG. 14 is a schematic, plan view of a portion of a microfluidic ejection element, showing a pre-determined firing sequence.

The pre-determined firing sequence of nozzles may be selected to, for example, avoid having adjacent nozzles firing sequentially. In this way, interference (sometimes referred to as fluidic crosstalk) from one nozzle to an adjacent nozzle may be avoided. An example of such an arrangement is shown in FIG. 14. As an illustrative example only, FIG. 14 illustrates nozzles fired in sequence that have six unfired nozzles physically interposed between them.

Figure 15:
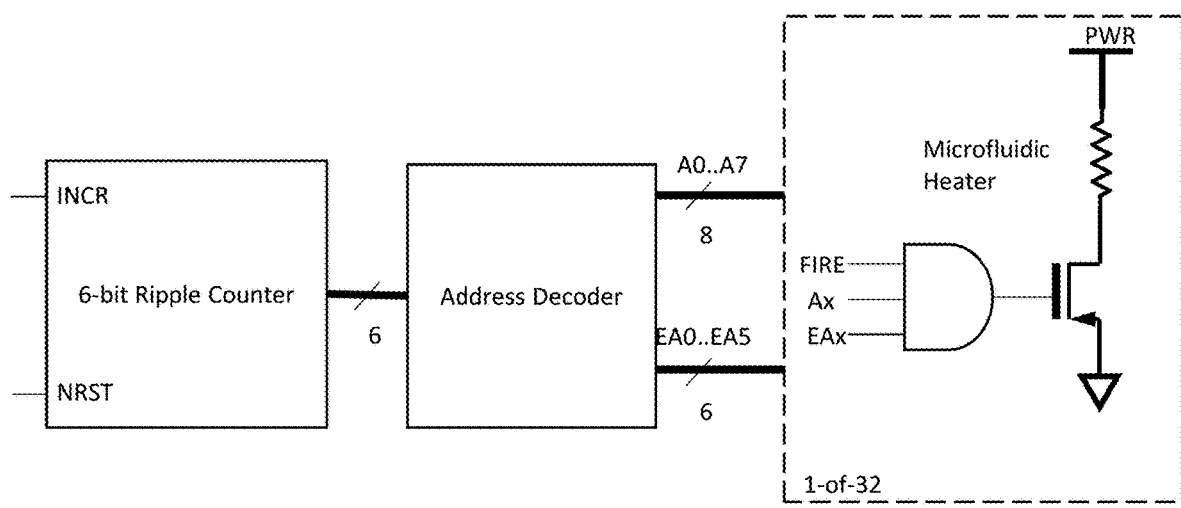
FIG. 15 is an exemplary logic circuit diagram.

The microfluidic ejection element comprises a control circuit further comprising a logic circuit for selecting nozzles from a sequence, and additional analog circuitry. An exemplary logic circuit is illustrated in FIG. 15. The external INCR signal drives a 6-bit ripple counter. The ripple counter is configured to reset to a count of one (1) when reaching its terminal count, where the terminal count may be less than $2^6-1$, for example. The terminal count may be selected to be equal to the number of nozzles physically present on the chip. The ripple counter is coupled to an address decoder, which may output a set of address lines (Ax) and extended address lines (EAx). The decoded addresses and extended addresses may be configured to select a particular heater. FIG. 15 illustrates an exemplary microfluidic ejection element having thirty-two thermal actuators 114 that that may be physically addressed, and the additional addresses are unused.

Figure 16:
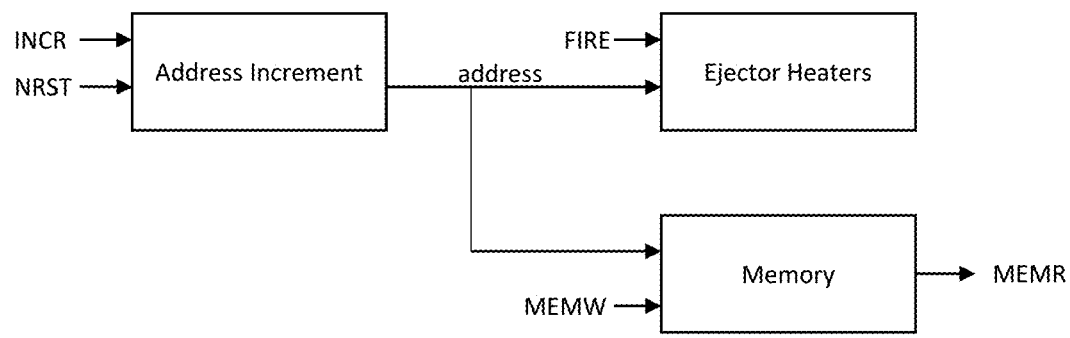
FIGS. 16 and 17 are exemplary logic circuit diagrams, including addressing memory cells.

With reference to FIG. 16, in a normal operation of the microfluidic ejection element, only two signals are used to perform the dispensing of fluid, INCR and FIRE. The INCR and FIRE signals are used in an alternating sequence to advance to the next nozzle in the pre-determined sequence, and to activate the thermal actuator. This allows the use of a small and unsophisticated controller, or to reduce the computational workload on the controller.

The address decoder may be configured to actuate only one nozzle at a time. Or, the address decoder may actuate many nozzles simultaneously, allowing a higher dispensing rate.

The described interface is not dependent on the number of nozzles. While having knowledge of the number of nozzles present is useful to provide a sufficient time for refill of the fluid chambers 122, the interface need not change when the cartridge is reconfigured with a different number of nozzles. Indeed, if the number of nozzles is supplied to the controller at the time of cartridge insertion, the controller may be compatible with future cartridges having different numbers of nozzles without requiring any upgrade.

The energy dissipated by the thermal actuator may be determined by the duration of the pulse applied to the FIRE signal. In this case, the driving source of the FIRE signal must have precise timing. Alternatively, the timing of the pulse applied to the thermal actuator may be determined by the configuration of the chip, and so the timing of the driving source of the FIRE signal is non-critical.

Figure 17:
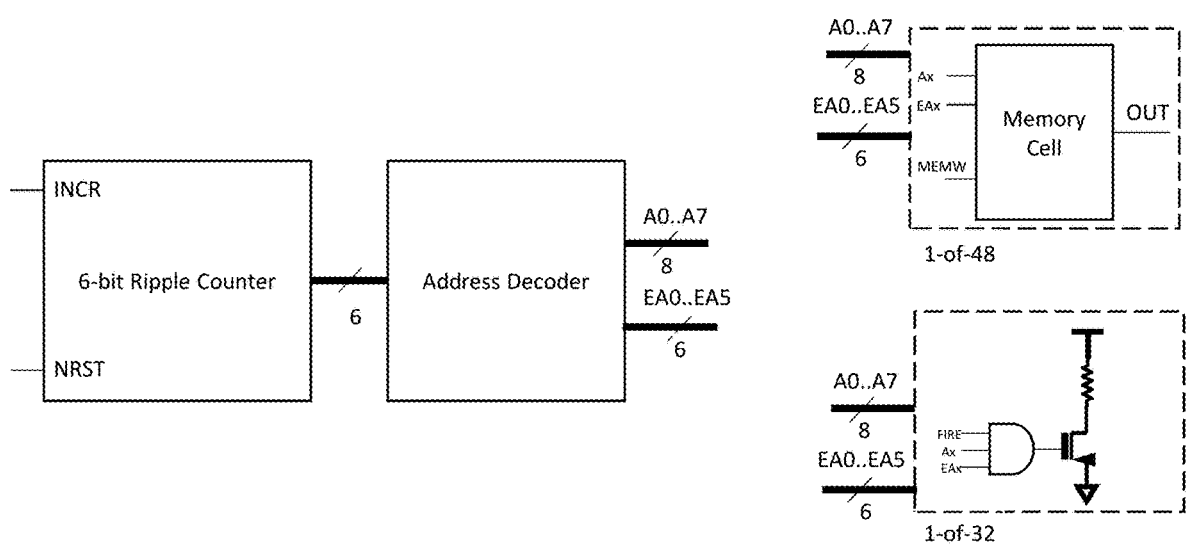
Figure 18:
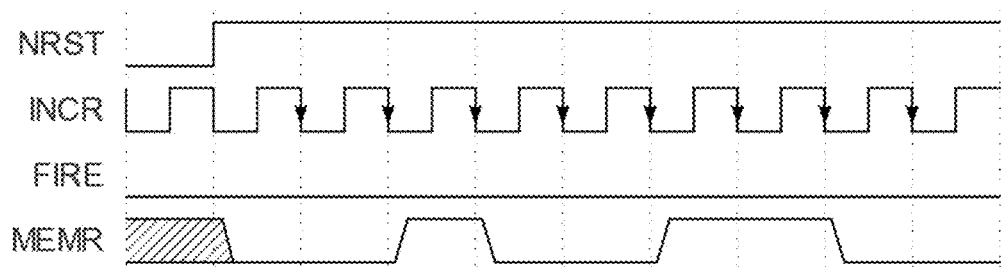
FIG. 18 is a timing diagram for the simplified interface of the present disclosure.

The microfluidic ejection element may additionally comprise embedded memory cells, such that information may be stored during manufacture or during end use. For example, a logic circuit such as shown in FIGS. 16 and 17 could be used to access individual memory bits from a sequence of memory bits as well as thermal actuators. In this example, the decoded addresses are sufficient to address all 48 bits of memory. In this example, the entire contents of the memory embedded in the ejection chip could be read out by repeatedly toggling the INCR signal, while monitoring the MEMR signal of FIG. 13. As individual memory cells are sequentially addressed by the internal logic, the corresponding bit of data is presented on MEMR. The value of the memory bit of data is presented on an output pin corresponding to signal MEMR. The memory cell may be a one-time programmable memory bit, such as a fusible metal alloy. An electrical interface may be provided which translates the state of conduction of the fuse into an open drain electrical output. An example waveform which represents reading data from the interface is shown in FIG. 18.

Similarly, a particular bit of memory could be written by toggling the INCR signal until the desired memory bit is selected, and then asserting the MEMW signal. The value to be written to a memory bit is applied to an input pin corresponding to the MEMW signal.

Examples of data stored on the chip may include the identity of the fluid composition disposed in the cartridge, the firing parameters needed by the control logic to properly operate the microfluidic ejection element, or the estimated amount of fluid composition remaining in the cartridge during usage. If the number of nozzles present on the chip is recorded in the memory, the controller element would not have to embed further details about the construction of the microfluidic ejection element, allowing for future version that have more or fewer nozzles.

Figure 19:
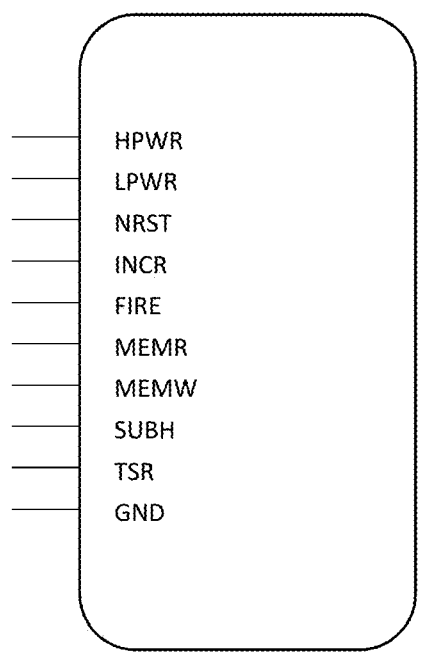
FIG. 19 is a diagram of a interface to a microfluidic ejection element.
Figure 20:
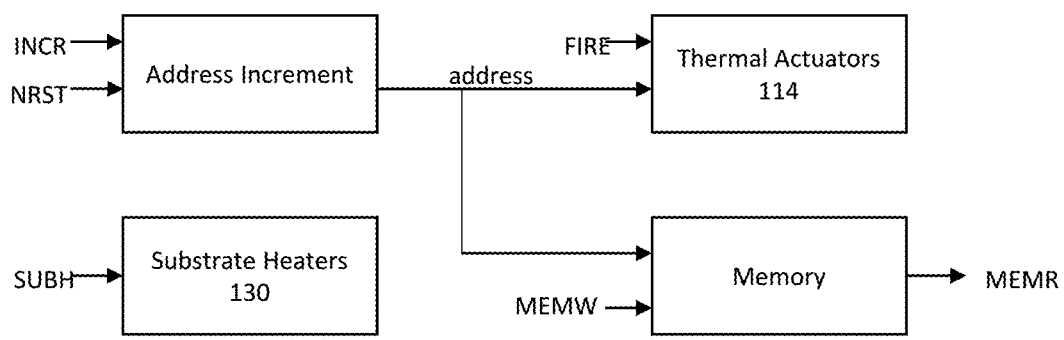
FIG. 20 is an exemplary logic circuit diagram, including addressing substrate heaters and memory cells.

With reference to FIGS. 11, 19, and 20, in applications where it is desirable to control the temperature of the ejection chip, a substrate heater(s) 130 may be built into the microfluidic ejection element which is distinct from the thermal actuators 114 used for heating of the fluid composition. The substrate heater(s) 130 are designed to raise the temperature of the entire microfluidic ejection element within a prescribed time. The substrate heater(s) may be controlled by a digital signal, which is labeled SUBH in FIGS. 19 and 20.

For accurate temperature control, it may be desirable to include a temperature sensing element on the microfluidic ejection element. The temperature sensing element could be, for example, a metal alloy resistive strip, where the temperature coefficient of resistivity is well characterized. Measurement of the temperature via the sensing element could be done via the analog signal available on the TSR signal of FIG. 19. Continuing the example of the metal alloy resistive strip as the temperature sensor, external circuitry such as a Wheatstone bridge could be provided to translate the temperature dependence of resistance to an analog voltage.

FIG. 19 also shows additional connections that may be used to complete the physical interface to the microfluidic dispensing element. In FIG. 19, HPWR is the power input for actuating the thermal actuators and opening the memory fuses. Depending on the construction of the element, HPWR may be in the range 6V to 18V. LPWR is the power input for the counting and decoding circuitry, and may be in the range 3.3V to 5V. GND is the common current return path for the power supplies.

Figure 21:
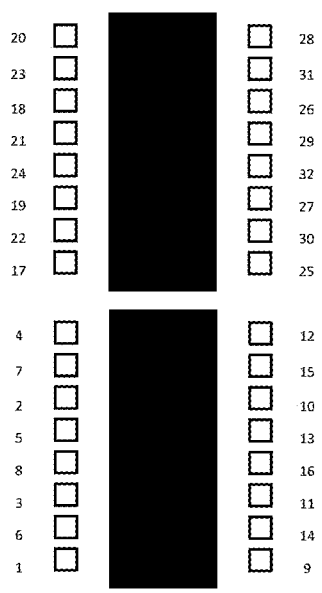
FIG. 21 is a schematic, plan view of a portion of a microfluidic ejection element, showing a pre-determined firing sequence for a cartridge having two fluid composition reservoirs.

It may be desirable to construct a microfluidic dispensing cartridge having two fluid composition reservoirs. This allows delivery of two fluid compositions either simultaneously or at different times. The simplified interface described here could be easily adapted to this configuration. FIG. 21 shows how arrays of nozzles may be grouped around multiple fluid paths in a two-channel ejection chip. In this example, a first fluid may be dispensed by firing only the first 16 nozzles in sequence. Following this, a second fluid may be dispensed by firing the subsequent 16 nozzles, which are arrayed around the second fluid path. Alternatively, following dispensing of the first fluid, the chip could be reset via the NRST signal, so in subsequent firings the first fluid is dispensed again. If the only second fluid is to be dispensed, the controller would toggle the INCR signal 16 times (without activating the FIRE signal) to advance to the second group of nozzles. Thereafter, the INCR and FIRE signals would be used alternately to increment and fire nozzles containing the second fluid.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of delivering a fluid composition from a thermally-activated microfluidic ejection element, the thermally-activated microfluidic ejection element comprising a plurality of nozzles and a thermal actuator associated with each nozzle, the method comprising:
   connecting the thermally-activated microfluidic device to a power source;
   delivering a first electrical pulse to a first input in communication with a logic-based counter and address decoder, the logic-based counter and address decoder selecting a thermal actuator in a sequence that is predetermined;

supplying a second electrical pulse of a well-defined width to a second input to activate the selected thermal actuator; and ejecting a fluid composition from the nozzle associated with the selected thermal actuator.

2. The method of claim 1 further comprising the step of reading a memory bit from a sequence of memory bits, wherein the value of the memory bit is presented on an output pin.

3. The method of claim 2, wherein the number of memory bits and the number of nozzles are not equal.

4. The method of claim 1 further comprising the step of writing a memory bit currently selected from a sequence of memory bits.

5. The method of claim 1, wherein the the logic-based counter is a ripple counter.

6. The method of claim 1, wherein the sequence of nozzles is arranged on the thermally-activated microfluidic ejection element such that nozzles that are numerically adjacent in the sequence are not physically adjacent.

7. The method of claim 1, wherein a first plurality of nozzles is in fluid communication with a first fluid composition disposed in a first reservoir, wherein a second plurality of nozzles is in fluid communication with a second fluid composition disposed in a second reservoir, wherein the first and second fluid compositions are different.

8. The method of claim 1, wherein the duration of the second electrical pulse corresponds to the time that the thermal actuator associated with the selected nozzle is activated.

9. The method of claim 1, wherein the first electrical pulse selects two or more thermal actuators from a pre-determined sequence, and wherein the second electrical pulse activates the two or more thermal actuators, and wherein the step of ejecting a fluid composition from the nozzle associated with the thermal actuator further comprising ejecting a fluid composition from the nozzles associated with the two or more thermal actuators.

10. The method of claim 1 further comprising the steps of:
raising the temperature throughout the thermally-activated microfluidic ejection element with a substrate heater that is separate from the thermal actuator associated with the nozzle.

11. The method of claim 10 further comprising the step of measuring the temperature of the thermally-activated microfluidic ejection element.

12. The method of claim 1 further comprising the steps of:
delivering a third electrical pulse to the first input, wherein the logic-based counter and address decoders elect a second thermal actuator from the sequence;

supplying a fourth electrical pulse of a well-defined width to the second input to activate the second selected thermal actuator; and ejecting a fluid composition from the second nozzle associated with the second selected thermal actuator.

\* \* \* \* \*